United States Patent
Freitag et al.

(10) Patent No.: US 10,074,489 B2
(45) Date of Patent: Sep. 11, 2018

(54) SOLID STATE HOLE TRANSPORT MATERIAL

(71) Applicant: Dyenamo AB, Täby (SE)

(72) Inventors: Marina Freitag, Uppsala (SE); Quentin Daniel, Lacanau (FR); Gerrit Boschloo, Uppsala (SE); Licheng Sun, Vallentuna (SE)

(73) Assignee: Dyenamo AB, Taby (SE)

( * ) Notice: Subject to any disclaimer, the term of this patent is extended or adjusted under 35 U.S.C. 154(b) by 0 days.

(21) Appl. No.: 15/503,270

(22) PCT Filed: Apr. 20, 2015

(86) PCT No.: PCT/EP2015/058501
§ 371 (c)(1),
(2) Date: Feb. 10, 2017

(87) PCT Pub. No.: WO2016/023644
PCT Pub. Date: Feb. 18, 2016

(65) Prior Publication Data
US 2017/0236650 A1  Aug. 17, 2017

(30) Foreign Application Priority Data
Aug. 11, 2014 (EP) .................................... 14180515

(51) Int. Cl.
| | |
|---|---|
| *C07F 1/08* | (2006.01) |
| *H01L 51/50* | (2006.01) |
| *H01G 9/20* | (2006.01) |
| *H01L 51/00* | (2006.01) |
| *H01L 51/42* | (2006.01) |
| *H01L 51/05* | (2006.01) |

(52) U.S. Cl.
CPC .................. *H01G 9/20* (2013.01); *C07F 1/08* (2013.01); *H01L 51/006* (2013.01); *H01L 51/0091* (2013.01); *H01L 51/0056* (2013.01); *H01L 51/0512* (2013.01); *H01L 51/42* (2013.01); *H01L 51/5056* (2013.01)

(58) Field of Classification Search
CPC .................................... C07F 1/08; H01L 51/50
USPC ............................... 546/10, 2; 313/504, 498
See application file for complete search history.

(56) References Cited

U.S. PATENT DOCUMENTS
2011/0073172 A1  3/2011 LeSuer et al.

FOREIGN PATENT DOCUMENTS
| | | |
|---|---|---|
| WO | WO 2011/120709 A1 | 10/2011 |
| WO | WO 2012/114316 A1 | 8/2012 |

OTHER PUBLICATIONS

Edwin C. Constable et al, "Copper (I) complexes of 6, 6' -disubstituted 2,2' -bipyridine dicarboxylic acids: new complexes for incorporation into copper-based dye sensitized solar cells (DSCs)," Dalton Transactions, No. 33, Jan. 1, 2009, pp. 6634-6644.
International Search Report mailed by European Patent Office dated May 19, 2015 in the corresponding PCT Application No. PCT/EP2015/058501.
Written Opinion mailed by European Patent Office dated May 19, 2015 in the corresponding PCT Application No. PCT/EP2015/058501.

*Primary Examiner* — Charanjit Aulakh
(74) *Attorney, Agent, or Firm* — Knobbe, Martens, Olson & Bear, LLP

(57) ABSTRACT

A solid or quasisolid state hole transport material (HTM) includes the following complex:

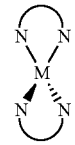

in which M is copper (Cu), palladium (Pd), gold (Au), silver (Ag), nickel (Ni), vanadium (V) cobalt (Co); and each structure represents an at least 6,6' disubstituted 2,2'-bipyridine, or an at least 2,9 disubstituted 1,10-phenanthroline Electronic devices, such as solar cells can include the solid or quasisolid state HTM, in which the complex is the main hole conducting compound of the HTM.

20 Claims, 2 Drawing Sheets

SOLID STATE HOLE TRANSPORT MATERIAL

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present invention relates to the field of electronic devices, such as organic electronic devices, and hole transport materials useful in such devices.

BACKGROUND OF THE INVENTION

Hole conducting- and/or hole transport materials are useful in a wide range of electronic devices and applications, such as in organic electroluminescent (EL) devices, organic light-emitting devices (OLEDs) and in solar cells.
Dye-Sensitized Solar Cells A dye-sensitized solar cell (DSC, also sometimes referred to as DSSC or DYSC) is a particular type of solar cell in which a hole transport material (HTM) may prove useful. DSCs have gained a great interest as cost-effective alternatives to silicon-based photovoltaic devices. In the DSC, light is absorbed by a dye molecule anchored to a mesoporous wide band-gap semiconductor, normally $TiO_2$. Upon light absorption the photoexcited dye injects an electron into the conduction band of the semiconductor and its resulting oxidized state is regenerated by a redox mediator in a surrounding electrolyte. So far the best cell performances in DSCs obtained with ruthenium based dyes and the iodide/triiodide redox couple have been about 11% conversion efficiency.
Copper Based HTMs Fukuzumi and coworkers (*Journal of the American Chemical Society*, 2005, 127(26):9648-9654) have constructed the first dye-sensitized solar cells using copper complexes as redox couples to compare the photoelectrochemical responses with those using the conventional $I_3^-/I^-$ couple. The maximum η value attained was 2.2% for DSC using $[Cu(dmp)_2]^{2+/+}$ under the weak solar light irradiation of 20 $mW/cm^2$ intensity.

In addition, Peng Wang and coworkers (*Chemical Communications*, 2011, 47(15):4376-4378) have employed a bis(2,9-dimethyl-1,10-phenanthroline) copper(I/II) redox shuttle demonstrating a 7.0% efficiency. DSCs free of a corrosive iodine electrolyte were demonstrated by Wang et al by virtue of a mesoporous titania thin-film, coated with a high-absorption-coefficient organic photosensitizer. However, the utilized copper redox shuttle was also found to display very low electron transfer rates on several noble metals, carbon black and conducting oxides, resulting in a poor fill factor.

CuI and CuSCN can be used as a solution-processable, inorganic hole conductor in solid state DSCs (ssDSCs) and methylammonium lead iodide perovskite solar cells. These solar cells can provide power conversion efficiencies as high as 6.0% for DSCs and show to be very stable, providing a better phorcurrent stability and fill factors in comparison with spiroOMeTAD based solar cells upon continuous 2 h illumination. However, despite these advantages, the efficiency obtained with CuI is still lower because of the exceptionally high voltages (Voc) obtained in spiro-OMeTAD solar cells. Future studies are aimed toward determining whether the high recombination seen in CuI-based solar cells can be reduced and higher Voc obtained. Despite these potential difficulties, CuI represents a promising low-cost hole conductor for perovskite solar cells.

US 2006/008580 discloses organic hybrid solar cells in which copper based organometallic complexes may be used as HTMs. The organic hybrid solar cells further comprises a substrate material, an electrode material, a dye material, and a semiconductive oxide layer, and the semiconductive oxide layer of the organic hybrid cell has been vapor deposited.

The high efficiency obtained with hybrid solar cells based on dye and/or perovskite sensitizers demonstrate their potential for implementation as commercial solar cells. However, the use of organic hole conductors may represent a potential hurdle to the future commercialization of this type of solar cell because of their relatively high cost. For example, the current commercial price of high purity spiro-OMeTAD is over ten times that of gold and platinum. While increased demand would undoubtedly lower this cost dramatically in any large scale commercial endeavor, it is likely to remain expensive due to the synthetic methods and high purity needed for photovoltaic applications. Thus, development of alternative hole conductors and/or HTMs is a promising avenue to further improve the performance of solar cells, as spiro-OMeTAD likely does not represent the ideal hole-conducting material for this system. Thus, in order to increase the efficiency of ssDSSC and to decrease their cost, a new kind of hole conducting material and/or HTM is required.

SUMMARY OF THE INVENTION

It is an object of the present invention to provide novel hole transport materials which overcome at least some of the deficiencies of prior art hole transport materials. It is a further object of the present invention to provide electronic devices comprising such novel hole transport materials. In particular, it is an object to provide novel solar cells comprising said novel hole transport materials. It is a further object of the present invention to provide novel hole conducting- and/or hole transport materials which may be produced at a lower cost than presently available hole conducting- and hole transport materials and which preferably display improved characteristics and performance when used in electronic applications and devices.

These objects are achieved, according to a first aspect of the invention, by the provision of a solid or quasisolid state hole transport material (HTM) comprising the complex of Formula I:

wherein M is selected from copper (Cu), palladium (Pd), gold (Au), silver (Ag), nickel (Ni), vanadium (V) and cobalt (Co); and each structure

represents an at least 6,6' disubstituted 2,2'-bipyridine, or an at least 2,9 disubstituted 1,10-phenanthroline. In some embodiments, the HTM comprises a mixture of two or more complexes of Formula I. In a preferred embodiment, the complex of Formula I, or a mixture of two or more complexes of Formula I, is the main hole conducting compound in the HTM.

According to another aspect, there is provided an electronic device comprising solid or quasisolid state hole transport material (HTM) according to the first aspect of the invention.

According to another aspect, there is provided the use of the complex of Formula I as a hole transport material in a solid state electronic device. In a preferred embodiment, the complex of Formula I, or a mixture of two or more complexes of Formula I, is used as the main hole transport material in a solid state electronic device. In an embodiment, the hole transport material (HTM) according to the first aspect of the invention is used as a hole transport material in a solid state electronic device.

The solid or quasisolid state HTM according to Formula I provides characteristics such as stability and high efficiency, in terms of e.g. photocurrent density-voltage (J-V) characteristics, to an electronic device in which it may be used for its hole conducting properties. The solid or quasisolid state HTM may also provide further advantages since it may dispense with the need for a blocking layer in an electronic device, such as a solar cell, where it is used. When utilized in electronic devices such as solar cells, the solid or quasisolid state HTM can easily be sensitized with a high atom economy. The HTM as disclosed herein can be prepared from commercially available components and may readily be made in a two step synthesis.

Each of the following individual embodiments accounted for below relate, unless specified otherwise, to all aspects of the present invention.

The HTM of the invention is preferably a metal-organic HTM. In other words, the HTM comprises both an inorganic component, such as a metal or metal ion, and an organic component.

In some embodiments, the complex is represented by the Formula II:

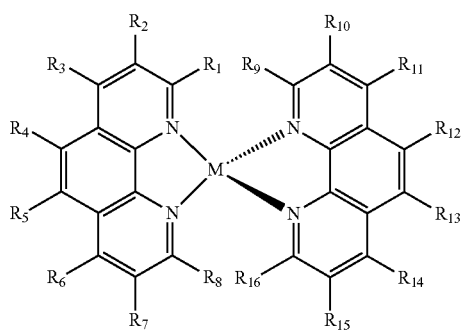

wherein each of $R_1$, $R_8$, $R_9$, and $R_{16}$ independently represents a group other than H, and each of $R_2$-$R_7$ and $R_{10}$-$R_{15}$ independently represents H.

In some embodiments, the complex is represented by the Formula III:

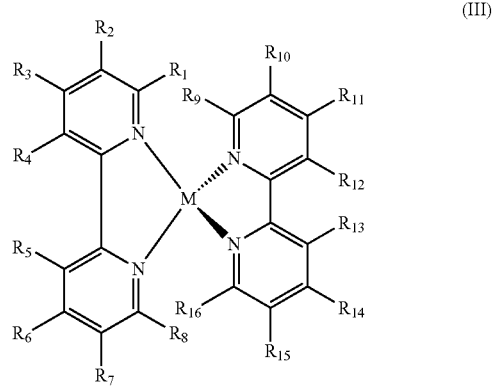

wherein each of $R_1$, $R_8$, $R_9$, and $R_{16}$ independently represents a group other than H, and each of $R_2$-$R_7$ and $R_{10}$-$R_{15}$ independently represents H.

The advantageous characteristics of the HTM may to at least some extent be dependent upon a distorted tetragonal geometry of the complex. Some non-linear molecular systems in a degenerate electronic state will be unstable and will undergo distortion to form a system of lower symmetry and lower energy and become stable. It is often encountered in octahedral complexes of the transition metals and is very common in, for example, six-coordinate copper(II) complexes. The distorted tetragonal geometry may for example comprise so-called Jahn-Teller distortion, which describes the geometrical distortion of molecules and ions that is associated with certain electron configurations. The distorted tetragonal geometry may for example imply that the structural change between the different redox states of the metal complexes, e.g. between M(I) and M(II) or between M(II) and M(III), is minimized.

In an embodiment, the complex has a distorted tetragonal geometry.

In an embodiment, $R_1$, $R_8$, $R_9$, and $R_{16}$ are independently of each other selected from the group of substituted and non-substituted, branched and unbranched, alkyl and aryl groups. In the bipyridine compound mentioned herein, $R_1$, $R_8$, $R_9$, and $R_{16}$ respectively are present in positions 6 and 6'. In the phenathroline compound mentioned herein, $R_1$, $R_8$, $R_9$, and $R_{16}$ respectively are present in positions 2 and 9.

Said group of substituted and non-substituted, branched and unbranched, alkyl and aryl groups should be understood as including, as non-limiting examples, an alkyl group, a substituted alkyl group, aliphatic cyclic group, aromatic group.

The above alkyl group and substituted alkyl group include methyl, ethyl, propyl, butyl, sec-butyl, tert-butyl, pentyl, hexyl, heptyl, octyl, stearyl, trichloromethyl, cyclopropyl, cyclohexyl, 1,3-cyclohexadienyl, 2-cyclopenten-1-yl and 2,4-cyclopentadien-1-ylidenyl.

In an embodiment at least one, preferably at least two, more preferably at least three and most preferably all four of $R_1$, $R_8$, $R_9$, and $R_{16}$ are selected from the group consisting of substituted and non-substituted, branched and unbranched, alkyl and aryl groups, preferably is a lower alkyl, more preferably methyl.

In an embodiment at least one, preferably at least two, more preferably at least three and most preferably all four of $R_1$, $R_8$, $R_9$, and $R_{16}$ are methyl groups.

In the inventive HTM, the complex of Formula I, which may also include a mixture of two or more complexes of Formula I, is used as a hole conducting compound. The complex(es) of Formula I is preferably the main hole conducting compound in the HTM. By "main hole conducting compound" it is meant that the HTM comprises more, by weight, of the complex(es) of Formula I, than ofther hole conducting compounds. As such, the complex of Formula I should be present in a sufficiently high concentration in the solid or quasisolid HTM to act as a hole conductor, and preferably as the main hole conductor. Accordingly, the complex(es) of Formula I typically constitute at least 50% by weight of the hole conducting compounds present in the HTM. At lower concentrations of the complex(es) of Formula I in the HTM, the complex may not be the main hole conductor.

In some embodiments the HTM comprises at least 20% by weight, such as at least 30%, 40%, 50%, 60%, 70% by, 80%, 90% or 95% by weight, of complex(es) of Formula I, based on the total weight of the HTM. In some embodiments the HTM comprises in the range of 20 to 100% by weight, 30 to 100% by weight, 40 to 100% by weight, 50 to 100% by weight, 60 to 100% by weight, 70 to 100% by weight, 80 to 100% by weight, or 90 to 100% by weight of the complex(es) of Formula I, based on the total weight of the HTM. In some embodiments the HTM comprises in the range of 20 to 90% by weight, 20 to 80% by weight, 20 to 70% by weight, 20 to 60% by weight, 20 to 50% by weight, 20 to 40% by weight, or 20 to 30% by weight, of the complex(es) of Formula I, based on the total weight of the HTM.

In some embodiments the HTM comprises in the range of 20 to 80% by weight, 30 to 70% by weight, or 40 to 60% by weight of the complex(es) of Formula I, based on the total weight of the HTM.

In some embodiments, the HTM consists, or essentially consists of the complex of Formula I. The term "consists of" as used herein means that the HTM is formed of the complex(es) of Formula I only, except for minor impurities or trace components. The term "essentially consists of" as used herein means that the HTM is comprised almost only of the complex(es) of Formula I, more particularly that the HTM comprises at least 90% or 95% by weight, of complex(es) of Formula I, based on the total weight of the HTM.

In addition to the complex(es) of Formula I, the HTM may also comprise other components. The portion of the HTM not made up of the complex of Formula I may for example comprise non hole conducting additives, including negative counter ions to the complex, metal salts (e.g. Li, Na, Co or Al) of the negative counter ions, solvent residues and synthesis byproducts of the complex of Formula I. These compounds may typically constitute up to 80% by weight of the HTM, based on the total weight of the HTM. Although the HTM may also comprise other hole conducting compounds, such other hole conducting compounds are only present in minor amounts, such that the complex(es) of Formula I is the main hole conducting compound in the HTM.

The complex of the HTM will typically be positively charged. In some embodiments, the HTM further comprises a negative counter ion to compensate the positive charge of the complex. The negative counter ion is preferably selected from the group consisting of $PF_6^-$ (hexafluorophosphate), $TFSI^-$ (bis(trifluoromethane) sulfonimide), $Cl^-$ (chloride) and $BF_4^-$ (tetrafluoroborate). In some embodiments the negative counter ion is selected from the group consisting of $PF_6^-$ (hexafluorophosphate) and $TFSI^-$ (bis(trifluoromethane) sulfonimide). In some embodiments the negative counter ion is $TFSI^-$ (bis(trifluoromethane) sulfonimide). The negative counter ion may constitute up to 80% by weight of the HTM, based on the total weight of the HTM. In some embodiments the HTM comprises in the range of 1 to 50% by weight or 5 to 30% by weight of a negative counter ion, based on the total weight of the HTM.

The HTM may further include various additives, e.g. for increasing the conductivity of the HTM. Additives may for example include an organic base to shift the conduction band of the semiconductor. In some embodiments, the HTM comprises a compound selected from the group consisting of 4-tert-butyl-pyridine (TBP), 1-methyl benzimidazole (NMBI) or 1-butyl benzimidazole (NBBI), The organic base may constitute up to 80% by weight of the HTM, based on the total weight of the HTM. In some embodiments the HTM comprises in the range of 10 to 60% by weight or 20 to 50% by weight of the organic base, based on the total weight of the HTM.

In embodiments of the aspects described herein, the HTM is in solid state. Thus, when used in an electronic device, the HTM may be present in solid state or form. This may be accomplished for example during preparation of the electronic device. The HTM may be applied in liquid form, e.g. as a layer, and then dried onto the device.

In some embodiments of the aspects described herein, said HTM is in quasisolid state. Quasisolid or semisolid is a physical term for something that lies along the boundary between a solid and a liquid, such as a gel. While similar to a solid in some respects, such as that quasisolids can support their own weight and hold their shapes, a quasisolid also shares some properties of liquids, such as conforming in shape to something applying pressure to it and the ability to flow under pressure. Thus, when used in an electronic device, the HTM may be present in a quasisolid state or form. This may be accomplished for example during preparation of the electronic device. The HTM may be applied in liquid form, e.g. as a layer, and then dried onto the device into a quasisolid state.

M is selected from copper (Cu), palladium (Pd), gold (Au), silver (Ag), nickel (Ni), vanadium (V) and cobalt (Co). In an embodiment, M is selected from Cu, Pd, Au, Ag and V. In a preferred embodiment, M is Cu. M is capable of assuming a reduced state and an oxidized state. M may be present in any available oxidation state or in a mixture of different oxidation states. Cu may for example be present as Cu(I) or Cu(II) or as a mixture of Cu(I) and Cu(II). Pd may for example be present as Pd(I) or Pd(II) or as a mixture of Pd(I) and Pd(II). Au may for example be present as Au(II) or Au(III) or as a mixture of Au(II) and Au(III). Ag may for example be present as Ag(I) or Ag(II) or as a mixture of Ag(I) and Ag(II). Ni may for example be present as Ni(I) or Ni(II) or as a mixture of Ni(I) and Ni(II). V may for example be present as V(III) or V(IV) or as a mixture of V(III) and V(IV). Co may for example be present as Co(II) or Co(III) or as a mixture of Co(II) and Co(III). Other oxidations states than those exemplified above may also be possible.

The metal complexes of the HTM typically have a distorted tetragonal geometry, implying that the structural change of the complex between the different oxidation states of M, e.g. between M(I) and M(II) or between M(II) and M(III) is minimized.

In particular embodiments, M is Cu. In such instances, the HTM is a bipyridine or phenatroline based copper complex having a distorted tetragonal geometry, implying that the structural change between the Cu(I) and Cu(II) complexes is minimized.

In an embodiment, the HTM is M-(2,9-dimethyl-1,10-phenanthroline)$_2$, herein also denoted M(dmp)$_2$. When M is Cu the HTM is preferably Cu-(2,9-dimethyl-1,10-phenanthroline)$_2$, herein also denoted Cu(dmp)$_2$.

In an embodiment, the HTM is M-(6,6'-dimethyl-2,2'-bipyridine)$_2$, herein also denoted M(dmbp)$_2$. When M is Cu the HTM is preferably Cu-(6,6'-dimethyl-2,2'-bipyridine)$_2$, herein also denoted Cu(dmbp)$_2$.

The HTM of the present invention may be manufactured from commercially available starting materials with high conductivity as well as high thermal and electrochemical stability, resulting in a non-toxic material. These characteristics may prove beneficial in the development of efficient and (e.g. organic) electronic devices with high efficiency and at low cost. Since the HTMs allow for solution processing, vapor deposition, screen-printing, spin coating etc, the HTMs can be used for preparing large area photovoltaic cells and other organic electronics.

With regards to its hole conducting properties, the HTM may be used as a p-type semiconductor. As described above, it allows for manufacturing of (organic) electronic devices at a much lower cost compared to manufacturing of (organic) electronic devices using previously known hole conducting materials. Moreover, the hole conducting material may easily be sensitized. Also, in particular in embodiments where the hole conducting materials are copper-based, the materials are solution-processable, wide-band-gap semiconductors with potentially high conductivity and stability.

The potential electronic devices the HTM may be used in are many. They may be used in organic and inorganic electronic devices. In certain embodiments, they may be used in organic electronic devices, such as organic transistors, or in organic optoelectronic devices such as organic light emitting diodes (OLED), organic photodetectors and organic solar cells. The above lists of electronic devices should not be construed as limiting.

As demonstrated in the appended examples, the HTM may prove particularly useful in solar cells. The inventors contemplate use of the HTMs within a range of different solar cells; such as in hybrid solar cells, organic solar cells, and dye-sensitized solar cells (DSCs), such as solid state DSCs (ssDSCs). The inventors have demonstrated that use of copper dimethylphenanthroline or dimethylbipyridine as solid state HTMs improve photocurrent density in ssDSCs.

When said device is a solar cell, it may further comprise a substrate, a counterelectrode layer, a photosensitizer/perovskite layer, optionally a blocking layer, and a transparent semiconductor layer. The counterelectrode may preferably be selected from graphite, a carbon nano-tube electrode and poly(3,4-ethylenedioxythiophene) (PEDOT).

A ssDSC comprising a HTM according to the present invention may be prepared by the general steps of applying a blocking layer onto a (e.g transparent) conducting oxide (e.g. fluorine doped tin oxide, FTO) layer. Next, a metal oxide layer (e.g. nanoparticles, nanotubes, nanowires) is deposited onto the blocking layer. Subsequent to application, the metal oxide substrate may be treated with a photosensitizer or a perovskite layer in order to provide a layer of absorber material along the surface of the metal oxide. Preferred metal oxide materials are $TiO_2$, $SnO_2$, ZnO, $Sb_2O_3$, PbO, $Nb_2O_5$, $ZrO_3$, $CeO_2$, $WO_3$, $SiO_2$, $Al_2O_3$, $CuAlO_2$, $SrTiO_3$, $SrCu_2O_2$ or a complex oxide containing several of these oxides. Next, the HTM is applied to the metal oxide or the optional photosensitizer layer. The sensitized metal oxide is preferably coated with a constant thickness layer of HTM. This constant thickness layer may for example be applied by vapor deposition, spin-coating, spray-coating or solvent processing. A conducting buffer layer, e.g. of PEDOT, graphite, etc., and a metal layer, e.g. Ag, Au, Al, Ca or Mg, are deposited on top of the HTM to complete the device. Alternatively, PEDOT applied (e.g. electrodisposition) onto a FTO Glass substrate with a spacer of thermoplastic polymer (e.g. Surlyn) completes the device in a sandwich arrangement.

The solar cells can be one-substrate so-called monolithc devices. Such devices and technology for these are described in WO97/16838, WO 01/77237, WO2009/095233 and WO 2007110427, which descriptions are incorporated in its entirety in this description. In such monolithic solar cells, HTMs according to the present invention replaces the electrolyte in the monolithic devices.

The term "hole transport material", "hole conductor" or "hole conducting material" as used herein should be understood as a positive charge conducting medium. In the context of the present invention, the terms "hole transport material", "hole transport agent" "hole conductor", and hole conducting agent" are used interchangeably.

The solid or quasisolid state HTM according to the invention may also be seen as a solid or quasisolid state electrolyte. The term "solid or quasisolid state electrolyte" as used herein should be understood as materials with high ionic conductivity, either of cation or anion but not usually both, and with negligible electronic conductivity. They are the solid state equivalent of molten salts or strong liquid electrolytes. Sometimes, they are also called superionic conductors, fast ion conductors or optimised ionic conductors.

BRIEF DESCRIPTION OF THE DRAWINGS

These and other aspects of the present invention will now be described in more detail, with reference to the appended drawings, wherein.

DETAILED DESCRIPTION OF THE INVENTION

EXAMPLES

Example 1

Synthesis of Cudmp$_2$

All chemicals and solvents were purchased from Sigma-Aldrich, if not stated otherwise, and were used without further purification.

Cu(II)dmp$_2$Cl$_2$ (1): One equivalent of CuCl$_2$ was mixed with 4 equivalents of Neocuproine hydrate in ethanol, under nitrogen atmosphere, at room temperature for 2 hours. Complex (1) was collected by filtration and washed with water and diethyl ether. The yield was 80% (mol).

Cu(II)dmp$_2$Cl-TFSI (2): Complex (1) was dissolved in a 1:2 ethanol/water mixture. To this solution, 5 equivalents of Li-TFSI were added. The solution was stirred for 2 hours at room temperature under nitrogen atmosphere. Complex (2) was collected by filtration and washed with water and diethyl ether. The yield was 92% (mol).

Cu(I)dmp$_2$TFSI (3): Complex (2) was dissolved in acetonitrile. To this solution, 10 equivalents of ascorbic acid were added. The solution was stirred for 2 hours at room temperature under nitrogen atmosphere in diethyl ether. After filtration of the remaining ascorbic acid, the solvent was evaporated which provided complex (3) as a crude of dark red powder. After further purification, complex (3) was obtained as intense red powder. The yield was 90% (mol).

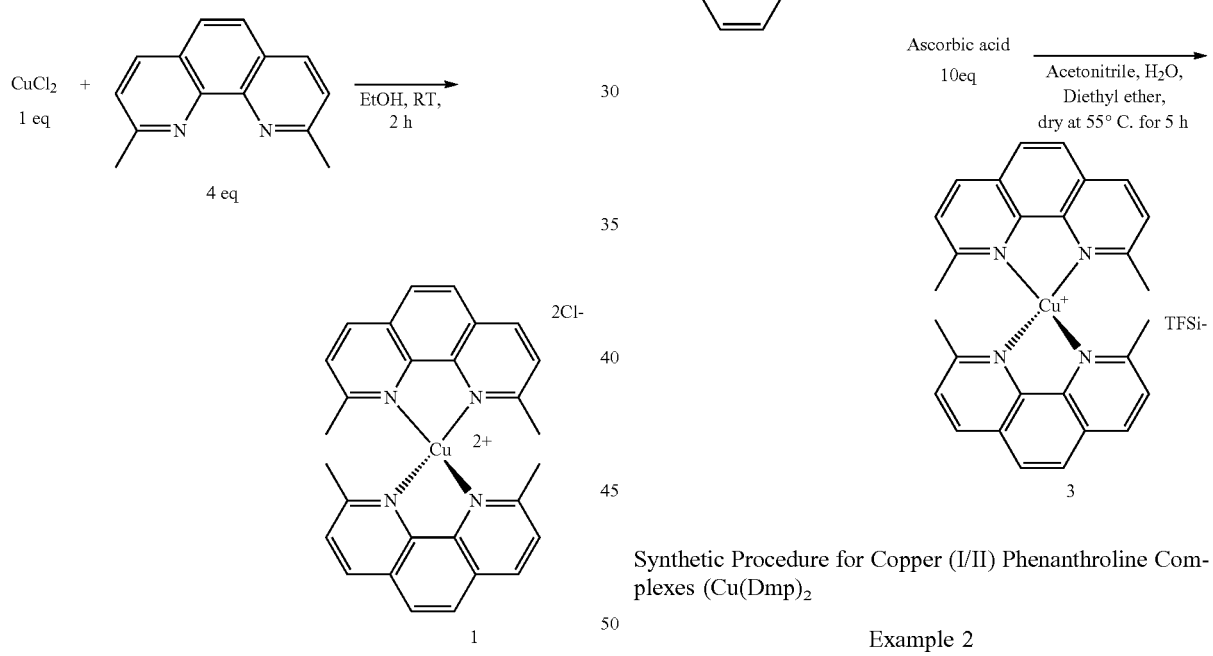

Synthetic Procedure for Copper (I/II) Phenanthroline Complexes (Cu(Dmp)$_2$

Example 2

Synthesis of Cudmbp$_2$

All chemicals and solvents were purchased from Sigma-Aldrich, if not stated otherwise, and were used without further purification.

Cu(II)dmbp$_2$Cl$_2$ (4): One equivalent of CuCl$_2$ was mixed with 2.2 equivalents of 2,2'-dimethyl bipyridine in ethanol and water (1:1), under nitrogen atmosphere, at room temperature for 2 hours. Complex (4) was collected by filtration and washed with water and diethyl ether. The yield was 80% (mol).

Cu(II)dmp$_2$Cl-TFSI (5): Complex (4) was dissolved in 1:2 ethanol/water mixture. To this solution, 5 equivalents of Li-TFSI were added. The solution was stirred for 2 hours at room temperature under nitrogen atmosphere. Complex (5)

was collected by filtration and washed with water and diethyl ether. The yield was 92% (mol).

Cu(I)dmbp$_2$TFSI (6): Complex (5) was dissolved in acetonitrile. To this solution, 10 equivalents of ascorbic acid were added. The solution was stirred for 2 hours at room temperature under nitrogen amosphere. After filtration of the remaining ascorbic acid, the solvent was evaporated which provided the crude of complex (6) as a dark red powder. After further purification complex (6) was obtained as intense red powder. The yield was 60% (mol).

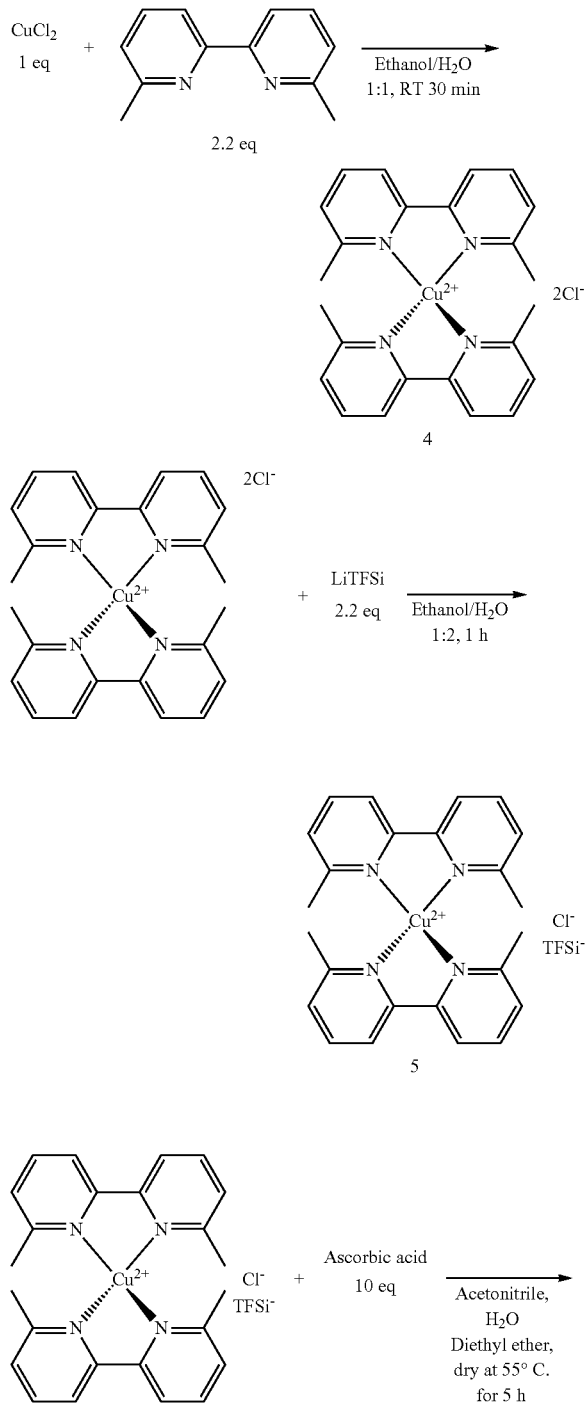

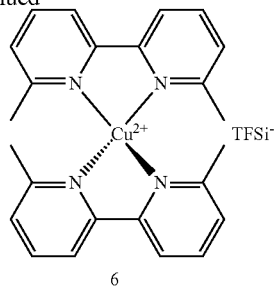

Synthetic Procedure for Copper (I/II) Dimethyl Bipyridine Complexes (Cu(dmbp)$_2$)

Example 3

Preparation of ssDSC Devices

Figure 1:
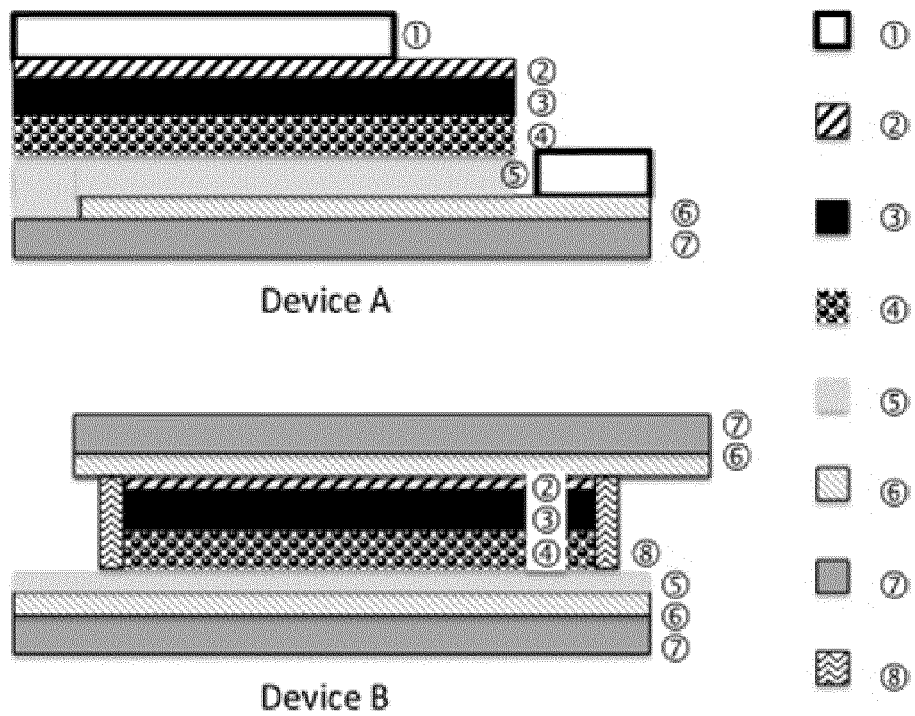
FIG. 1 is a schematic cross-sectional representation of the structures of the example solar cells (device A and B) according to the present invention. Device A comprises a metal contact (1), a conducting layer (2), a HTM (3), a photosensitizer/perovskite (4), a blocking layer (5) a FTO layer (6), and a glass/substrate (7). Device B has a sandwich structure of a glass/substrate (7), a FTO layer (6), a conducting layer (2), a HTM (3), a photosensitizer/perovskite (4), polymer/spacer (8), a blocking layer (5), a FTO layer (6), and a glass/substrate (7).

A ssDSC device is fabricated using metal oxide nanoparticles with attached photosensitizer or perovskite layer as the absorber layer, see FIG. 1 (Device A and B).

Briefly, a blocking layer (100-200 nm) is deposited on top of a transparent conducting oxide (FTO) layer to prevent ohmic contact between the HTM and FTO. Next, a metal oxide layer (for example in the form of nanoparticles, nanotubes, nanowires, etc) is deposited on top of the blocking layer. Subsequent to deposition, the metal oxide substrate is treated with a photosensitizer or a perovskite layer to afford a layer of absorber material along the surface of the metal oxide. Preferred metal oxide materials are $TiO_2$, $SnO_2$, ZnO, $Sb_2O_3$, PbO, $Nb_2O_5$, $ZrO_2$, $CeO_2$, $WO_3$, $SiO_2$, $Al_2O_3$, $CuAlO_2$, $SrTiO_3$, $SrCu_2O_2$ or a complex oxide containing several of these oxides. Next, an HTM as described herein is applied to the metal oxide/photosensitizer. The sensitized $TiO_2$ film is coated with a constant thickness layer of HTM, which can be applied by vapour deposition, or by solution process deposition, for example spin-coating or spray-coating of a HTM solution, followed by drying.

Then a conducting buffer layer of poly(3,4-ethylenedioxythiophene) (PEDOT) or graphite and a metal layer (Ag, Au, Al, Ca or Mg) is deposited on top of the HTM to complete the device (Device A) or with electrodeposited PEDOT on FTO Glass substrate with thermoplastic polymer (e.g. Surlyn) as spacer in a sandwich arrangement (Device B).

Example 4

Preparation of ssDSC Prototypes Based on Spiro-OMeTAD, Cudmp$_2$ and Cudmbp$_2$ as HTMs In this Example, an HTM composition including Cudmp$_2$ or Cudmbp$_2$ (Cu(I) 0.2 M and Cu(II) 0.05 M), 4-tert-butylpyridine (TBP, 0.5 M), lithium bis(trifluoromethanesulfonyl)imide (LiTFSI 0.1 M) in a mixture of chlorobenzene (CB) or acetonitrile (CH$_3$CN) was used. The different HTMs/electrolytes used are listed below in Table 1.

Each of the HTM compositions was dispersed onto $TiO_2$ nanoparticle substrates that had previously been soaked in a solution of photosensitizer (0.2 mM, LEG 4 in tert-butanol and acetonitrile). Following (Device B) a deposition of PEDOT/FTO (aq. Electropostion of PEDOT) electrode on top by melting Surlyn as a spacer.

TABLE 1

Tested HTM/electrolyte and structure of device

| No. | HTM/Electrolyte | Device A/B |
|-----|-----------------|------------|
| 1 | Cudmbp$_2$ HTM | B |
| 2 | Cudmbp$_2$ EL | B |
| 3 | Cudmp$_2$ HTM | B |
| 4 | Cudmp$_2$ EL | B |
| 5 | Spiro-OMeTAD | B |

Figure 2:
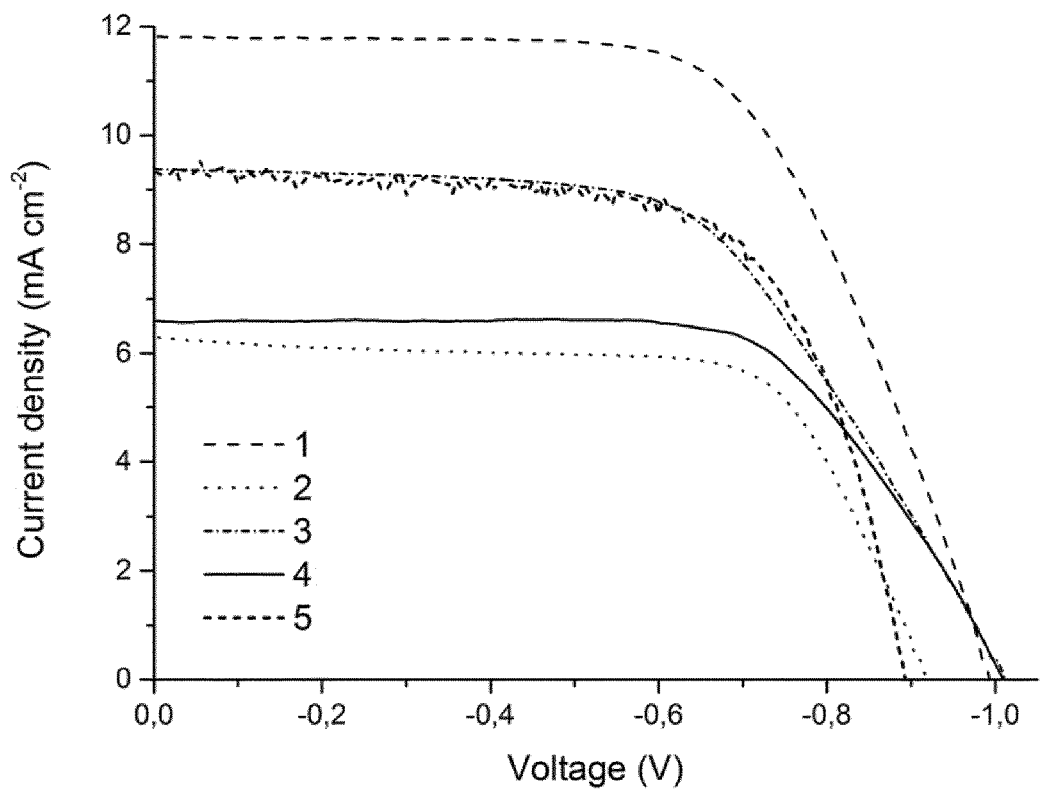
FIG. 2 is a diagram showing the current density vs. voltage characteristics (J-V characteristics) of DSCs comprising HTMs and liquid electrolytes of copper dimethyl phenanthroline, copper dimethybipyridine and Spiro-OMeTAD under irradiation of 100 mW cm$^{-2}$ simulated AM 1.5 sunlight.

The photocurrent density-voltage (J-V) characteristics of the DSCs and ssDSCs with the solid state HTMs and liquid electrolytes of copper dimethyl phenanthroline, copper dimethybipyridine and Spiro-OMeTAD were subsequently tested under 100 m W cm$^{-2}$ AM 1.5 illumination. The detailed photovoltaic parameters of the open circuit voltage ($V_{oc}$), fill factor (FF), short-circuit current density ($J_{SC}$) and photovoltaic conversion efficiency ($\eta$) are given in Table 2 as well as in FIG. 2.

TABLE 2

J-V characteristics of DSCs and ssDSCs

| No. | HTM/Electrolyte | $V_{oc}$ (mV) | $J_{sc}$ (mA/cm2) | FF | $\eta$ (%) |
|-----|-----------------|---------------|-------------------|------|------------|
| 1 | Cudmbp$_2$ HTM | 995 | 11.8 | 0.63 | 7.4 |
| 2 | Cudmbp$_2$ EL | 915 | 6.3 | 0.69 | 4.0 |
| 3 | Cudmp$_2$ HTM | 1010 | 9.4 | 0.62 | 6.8 |
| 4 | Cudmp$_2$ EL | 1010 | 6.6 | 0.67 | 4.5 |
| 5 | Spiro-OMeTAD | 895 | 9.4 | 0.67 | 5.6 |

As demonstrated in Table 2 above, use of copper dimethylphenanthroline or dimethylbipyridine as solid state HTMs improved the photocurrent density. The $J_{SC}$ of the DSC Cudmp$_2$ and Cudmbp$_2$ increased from 6.6 mA cm$^{-2}$ to 9.4 mA cm$^{-2}$ and 6.3 mA cm$^{-2}$ to 11.8 mA cm$^{-2}$ respectively, when Cudmp$_2$ and Cudmbp$_2$ were used as HTMs in ssDSC. Thus, the solid state HTMs show improvement both over the corresponding liquid HTMs and over Spiro-OMeTAD.

What is claimed is:

1. A solid or quasisolid state hole transport material (HTM) comprising the complex of Formula I:

(I)

wherein M is selected from copper (Cu), palladium (Pd), gold (Au), silver (Ag), nickel (Ni), vanadium (V) and cobalt (Co); and
each structure

consists of 6,6' disubstituted 2,2'-bipyridine wherein the substituents at the position 6 and 6' are independently selected from the group consisting of substituted and non-substituted, branched and unbranched, alkyl and aryl groups, or 2,9 disubstituted 1,10-phenanthroline wherein the substituents at the position 2 and 9 are independently selected from the group consisting of substituted and non-substituted, branched and unbranched, alkyl and aryl groups,
and wherein the HTM comprises the complex of Formula I more than other hole conducting compounds by weight.

2. The solid or quasisolid state HTM according to claim 1, wherein said complex of Formula I is represented by Formula II:

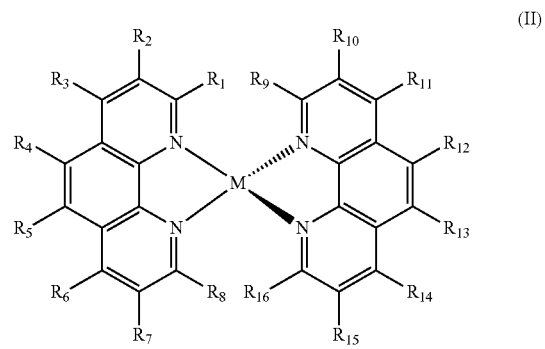

(II)

wherein each of $R_1$, $R_8$, $R_9$, and $R_{16}$ independently represents a group other than H, and
each of $R_2$-$R_7$ and $R_{10}$-$R_{15}$ independently represents H.

3. The solid or quasisolid state HTM according to claim 1, wherein said complex of Formula I is represented by Formula III:

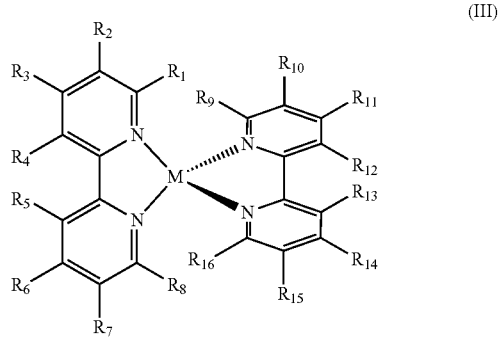

(III)

wherein each of $R_1$, $R_8$, $R_9$, and $R_{16}$ independently represents a group other than H, and
each of $R_2$-$R_7$ and $R_{10}$-$R_{15}$ independently represents H.

4. The solid or quasisolid state HTM according to claim 2, wherein each of $R_1$, $R_8$, $R_9$, and $R_{16}$ independently is selected from the group consisting of substituted and non-substituted, branched and unbranched, alkyl and aryl groups.

5. The solid or quasisolid state HTM according to claim 1, wherein M is selected from Cu, Pd, Au, Ag and V.

6. The solid or quasisolid state HTM according to claim 2, wherein said complex of Formula II is M-(2,9-dimethyl-1,10-phenanthroline)$_2$.

7. The solid or quasisolid state HTM according to claim 3, wherein said complex of Formula III is M-(6,6'-dimethyl-2,2'-bipyridine)$_2$.

8. The solid or quasisolid state HTM according to claim 1, further comprising a negative counter ion selected from the group consisting of PF6⁻ (hexafluorophosphate), TFSI⁻ (bis(trifluoromethane) sulfonimide), Cl⁻ (chloride) and BF⁻ (tetrafluoroborate).

9. The solid or quasisolid state HTM according to claim 1, wherein said complex of Formula I is in a solid state.

10. An electronic device comprising the solid or quasisolid state hole transport material (HTM) according to claim 1.

11. The electronic device according to claim 10, wherein said device is an organic electronic device, or a solar cell including, a hybrid solar cell, an organic solar cell, and/or a dye-sensitized solar cell (DSC).

12. The electronic device according to claim 10, wherein said device is a solid state dye-sensitized solar cell (ssDSC).

13. A method of producing an electronic device including a complex of Formula I:

(I)

wherein M is selected from copper (Cu), palladium (Pd), gold (Au), silver (Ag), nickel (Ni), vanadium (V) and cobalt (Co); and
each structure

consists of 6,6' disubstituted 2,2'-bipyridine wherein the substituents at the position 2 and 9 are independently selected from the group consisting of substituted and non-substituted, branched and unbranched, alkyl and aryl groups, or 2,9 disubstituted 1,10-phenanthroline wherein the substituents at the position 6 and 6' are independently selected from the group consisting of substituted and non-substituted, branched and unbranched, alkyl and aryl groups in a solid state electronic device, wherein the electronic device comprises the complex of Formula I more than other hole conducting compounds by weight.

14. The solid or quasisolid state HTM according to claim 2, wherein each of $R_1$, $R_8$, $R_9$, and $R_{16}$ independently is a lower alkyl.

15. The solid or quasisolid state HTM according to claim 2, wherein $R_1$, $R_8$, $R_9$, and $R_{16}$ are methyl.

16. The solid or quasisolid state HTM according to claim 1, wherein M is Cu.

17. The solid or quasisolid state HTM according to claim 2, wherein said complex of Formula II is Cu-(2,9-dimethyl-1,10-phenanthroline)$_2$.

18. The solid or quasisolid state HTM according to claim 3, wherein said complex of Formula III is Cu-(6,6'-dimethyl-2,2'-bipyridine)$_2$.

19. The electronic device according to claim 10, wherein said device is an organic light emitting diode (OLED) or an organic transistor.

20. The solid or quasisolid state HTM according to claim 1, wherein the HTM comprises at least 50% by weight of the complex of Formula I.

* * * * *